United States Patent
Reo et al.

(10) Patent No.: US 8,403,987 B2
(45) Date of Patent: Mar. 26, 2013

(54) PROSTHETIC INTERVERTEBRAL DISCS HAVING COMPRESSIBLE CORE ELEMENTS BOUNDED BY FIBER-CONTAINING MEMBRANES

(75) Inventors: Michael L. Reo, Redwood City, CA (US); Elizabeth V. Wistrom, Palo Alto, CA (US); Frank Fellenz, Los Gatos, CA (US); Thomas A. Afzal, Menlo Park, CA (US)

(73) Assignee: Spinal Kinetics Inc., Sunnyvale, CA (US)

( * ) Notice: Subject to any disclaimer, the term of this patent is extended or adjusted under 35 U.S.C. 154(b) by 0 days.

(21) Appl. No.: 11/528,099

(22) Filed: Sep. 27, 2006

(65) Prior Publication Data

US 2008/0077242 A1    Mar. 27, 2008

(51) Int. Cl.
*A61F 2/44* (2006.01)
(52) U.S. Cl. .................................................. 623/17.11
(58) Field of Classification Search .... 623/17.11–17.16; 606/61, 246–279
See application file for complete search history.

(56) References Cited

U.S. PATENT DOCUMENTS

| | | | |
|---|---|---|---|
| 3,867,728 A | 2/1975 | Stubstad | |
| 4,309,777 A | 1/1982 | Patil | |
| 4,623,574 A | 11/1986 | Harpell et al. | |
| 4,759,769 A | 7/1988 | Hedman et al. | |
| 4,911,718 A | 3/1990 | Lee et al. | |
| 4,932,969 A | 6/1990 | Frey et al. | |
| 5,002,576 A | 3/1991 | Fuhrmann et al. | |
| 5,039,519 A | 8/1991 | Inoue et al. | |
| 5,071,437 A | 12/1991 | Steffee | |
| 5,171,281 A | 12/1992 | Parsons et al. | |
| 5,221,431 A | 6/1993 | Choe et al. | |
| 5,221,432 A | 6/1993 | Choe et al. | |
| 5,314,477 A | 5/1994 | Marnay | |
| 5,370,697 A | 12/1994 | Baumgartner | |
| 5,456,722 A | 10/1995 | McLeod et al. | |
| 5,458,642 A | 10/1995 | Beer et al. | |
| 5,545,229 A | 8/1996 | Parsons et al. | |
| 5,609,634 A | 3/1997 | Voydeville | |
| 5,824,093 A * | 10/1998 | Ray et al. | 623/17.16 |
| 5,824,094 A * | 10/1998 | Serhan et al. | 623/17.16 |
| 5,827,328 A | 10/1998 | Buttermann | |
| 6,063,121 A | 5/2000 | Xavier et al. | |
| 6,113,638 A | 9/2000 | Williams et al. | |
| 6,156,067 A | 12/2000 | Bryan et al. | |
| 6,258,125 B1 | 7/2001 | Paul et al. | |
| 6,264,695 B1 | 7/2001 | Stoy | |
| 6,368,358 B1 * | 4/2002 | Glenn et al. | 8/115.6 |
| 6,402,785 B1 | 6/2002 | Zdeblick et al. | |
| 6,419,704 B1 | 7/2002 | Ferree | |

(Continued)

FOREIGN PATENT DOCUMENTS

WO    WO2005/011523    2/2005

OTHER PUBLICATIONS

Hudgins, Robert, "*Development and Characterization of a Prosthetic Intevertebral Disc,*" Thesis presented to the Academic Faculty, Georgia Institute of Technology (Nov. 1998).

(Continued)

*Primary Examiner* — Sameh Boles
(74) *Attorney, Agent, or Firm* — E. Thomas Wheelock (57) ABSTRACT

This description deals with a medical device, specifically a prosthetic intervertebral disc having a compressible core bounded by a fiber-containing or fiber-reinforced membrane.

18 Claims, 5 Drawing Sheets

U.S. PATENT DOCUMENTS

| | | | |
|---|---|---|---|
| 6,419,706 B1 * | 7/2002 | Graf | 623/17.16 |
| 6,436,137 B2 | 8/2002 | Wang et al. | |
| 6,447,543 B1 | 9/2002 | Studer et al. | |
| 6,527,803 B1 | 3/2003 | Crozet et al. | |
| 6,527,804 B1 | 3/2003 | Gauchet et al. | |
| 6,533,818 B1 | 3/2003 | Weber et al. | |
| 6,582,466 B1 | 6/2003 | Gauchet | |
| 6,582,468 B1 | 6/2003 | Gauchet | |
| 6,626,943 B2 * | 9/2003 | Eberlein et al. | 623/17.15 |
| 6,626,944 B1 | 9/2003 | Taylor | |
| 6,645,248 B2 * | 11/2003 | Casutt | 623/17.12 |
| 6,656,224 B2 | 12/2003 | Middleton | |
| 6,682,562 B2 * | 1/2004 | Viart et al. | 623/17.14 |
| 6,692,495 B1 | 2/2004 | Zacouto | |
| 6,726,721 B2 | 4/2004 | Stoy et al. | |
| 6,733,532 B1 | 5/2004 | Gauchet et al. | |
| 6,733,533 B1 | 5/2004 | Lozier | |
| 6,733,535 B2 | 5/2004 | Michelson | |
| 6,746,485 B1 | 6/2004 | Zucherman et al. | |
| 6,749,635 B1 | 6/2004 | Bryan | |
| 6,827,740 B1 | 12/2004 | Michelson | |
| 6,827,743 B2 | 12/2004 | Eisermann et al. | |
| 7,025,787 B2 | 4/2006 | Bryan et al. | |
| 7,060,097 B2 | 6/2006 | Fraser et al. | |
| 7,074,240 B2 | 7/2006 | Pisharodi | |
| 7,147,665 B1 | 12/2006 | Bryan | |
| 7,166,130 B2 | 1/2007 | Ferree et al. | |
| 7,220,282 B2 | 5/2007 | Kuslich | |
| 7,229,441 B2 | 6/2007 | Trieu et al. | |
| 7,291,150 B2 | 11/2007 | Graf | |
| 7,291,171 B2 * | 11/2007 | Ferree | 623/17.11 |
| 7,309,357 B2 | 12/2007 | Kim et al. | |
| 7,419,506 B2 * | 9/2008 | Hestad et al. | 623/17.16 |
| 7,563,284 B2 | 7/2009 | Coppes et al. | |
| 2002/0026244 A1 | 2/2002 | Trieu | |
| 2002/0111687 A1 | 8/2002 | Ralph et al. | |
| 2002/0128714 A1 | 9/2002 | Manasas et al. | |
| 2003/0028251 A1 | 2/2003 | Mathews | |
| 2004/0006343 A1 | 1/2004 | Sevrain | |
| 2004/0083002 A1 * | 4/2004 | Belef et al. | 623/17.16 |
| 2004/0143332 A1 | 7/2004 | Krueger et al. | |
| 2004/0193273 A1 * | 9/2004 | Huang | 623/17.12 |
| 2004/0243238 A1 * | 12/2004 | Arnin et al. | 623/17.12 |
| 2005/0021146 A1 * | 1/2005 | de Villiers et al. | 623/17.15 |
| 2005/0060036 A1 | 3/2005 | Schultz et al. | |
| 2005/0197702 A1 * | 9/2005 | Coppes et al. | 623/17.12 |
| 2005/0228500 A1 * | 10/2005 | Kim et al. | 623/17.13 |
| 2006/0129239 A1 | 6/2006 | Kwak | |
| 2007/0032875 A1 * | 2/2007 | Blacklock et al. | 623/17.15 |
| 2007/0168033 A1 * | 7/2007 | Kim et al. | 623/17.13 |

OTHER PUBLICATIONS

U.S. Appl. No. 60/403,356, Provisional Application, filed Aug. 15, 2002.

U.S. Appl. No. 60/403,402, Provisional Application, filed Aug. 15, 2002.

Spinal Kinetics, Inc.'s Preliminary Invalidity Contentions (USDC, Case No. 5:09-cv-01201, *Synthes USA et al.* v. *Spinal Kinetics, Inc.*, Sep. 8, 2009).

Spinal Kinetics, Inc.'s Preliminary Invalidity Contentions—Exhibit 8 (chart comparing claims of USP 7,429,270 to Baumgartner USP 5,370,697 in view of Stubstad USP 3,867,728 and Development and Characterization of a Prosthetic Intervertebral Disc, Robert Hudgins, Georgia Inst. of Tech., Nov. 1998).

Spinal Kinetics, Inc.'s Preliminary Invalidity Contentions—Exhibit 12 (chart comparing claims of USP 7,429,270 to Stubstad USP 3,867,728 in view of Development and Characterization of a Prosthetic Intervertebral Disc, Robert Hudgins, Georgia Inst. of Tech., Nov. 1998).

Spinal Kinetics, Inc.'s Preliminary Invalidity Contentions [Amended] (USDC, Case No. 5:09-cv-01201, *Synthes USA et al.* v. *Spinal Kinetics, Inc.*, Dec. 28, 2009).

Spinal Kinetics, Inc.'s Preliminary Invalidity Contentions [Amended]—Exhibit 10 (chart comparing claims of USP 7,429,270 to Baumgartner USP 5,370,697 in view of Stubstad USP 3,867,728 and Development and Characterization of a Prosthetic Intervertebral Disc, Hudgins, Georgia Inst. of Tech., Nov. 1998).

Spinal Kinetics, Inc.'s Preliminary Invalidity Contentions [Amended]—Exhibit 14 (chart comparing claims of USP 7,429,270 to Stubstad USP 3,867,728 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions (USDC, Case No. 5:09-cv-01201, *Synthes USA et al.* v. *Spinal Kinetics, Inc.*, Sep. 30, 2010).

Spinal Kinetics, Inc.'s Second Amended Preliminary Invalidity Contentions—Exhibit 1 (chart comparing claims of USP 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).

Spinal Kinetics, Inc.'s Second Amended Preliminary Invalidity Contentions—Exhibit 2 (chart comparing claims of USP 7,429,270 to Neuentwicklung eines lumbalen bewegungserhaltenden Bandscheibenimplantates, Feb. 25, 2002).

Spinal Kinetics, Inc.'s Second Amended Preliminary Invalidity Contentions—Exhibit 5 (chart comparing claims of USP 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).

Spinal Kinetics, Inc.'s Second Amended Preliminary Invalidity Contentions—Exhibit 6 (chart comparing claims of USP 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).

Spinal Kinetics, Inc.'s Second Amended Preliminary Invalidity Contentions—Exhibit 9 (chart comparing claims of USP 7,429,270 to Stubstad USP 3,867,728 in view of Optimal Design of Synthetic Intervertebral Disc Prosthesis Considering Nonlinear Mechanical Behavior, Kweon et al., Dec. 20, 2001).

Spinal Kinetics, Inc.'s Second Amended Preliminary Invalidity Contentions—Exhibit 10 (chart comparing claims of USP 7,429,270 to Stubstad 3,867,728 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 14 (chart comparing claims of USP 7,429,270 to Coppes USP 7,563,284 in view of Optimal Design of Synthetic Intervertebral Disc Prosthesis Considering Nonlinear Mechanical Behavior, Kweon et al., Dec. 20, 2001).

Spinal Kinetics, Inc.'s Second Amended Preliminary Invalidity Contentions—Exhibit 15 (chart comparing claims of USP 7,429,270 to Coppes USP 7,563,284 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 19 (chart comparing claims of USP 7,429,270 to Baumgartner USP 5,370,697 in view of Optimal Design of Synthetic Intervertebral Disc Prosthesis Considering Nonlinear Mechanical Behavior, Kweon et al., Dec. 20, 2001).

Spinal Kinetics, Inc.'s Second Amended Preliminary Invalidity Contentions—Exhibit 20 (chart comparing claims of USP 7,429,270 to Baumgartner USP 5,370,697 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 24 (chart comparing claims of USP 7,429,270 to Gauchet USP 6,733,532 in view of Optimal Design of Synthetic Intervertebral Disc Prosthesis Considering Nonlinear Mechanical Behavior, Kweon et al., Dec. 20, 2001).

Spinal Kinetics, Inc.'s Second Amended Preliminary Invalidity Contentions—Exhibit 25 (chart comparing claims of USP 7,429,270 to Gauchet USP 6,733,532 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 29 (chart comparing claims of USP 7,429,270 to Coppes USP 7,563,284 in view of Stubstad USP 3,867,728 further in view of Development and Characterization of a Prosthetic Intervertebral Disc, Hudgins, Georgia Inst. of Tech., Nov. 1998).

Burn et al., Neuentwicklung eines Implantates für den totalen Bandschiebenersatz, Vorgelegt von: Im Rahmen des Studiums für "Maschinenbau and Vergahrenstechnik" an der Eidgenöossischen Technischen Hochschule Zürich, im Feb. 2002).

English Translation of Burri et al., Neuentwicklung eines Implantates für den totalen Bandschiebenersatz, Vorgelegt von: Im Rahmen des Studiums für "Maschinenbau and Vergahrenstechnik" an der Eidgenöossischen Technischen Hochschule Zürich, im Feb. 2002), entitled Mechanical Engineering and Process Engineering at the Swiss Fedearl Institute of Technology Zurich (ETH Zurich) Feb. 2002.

Burn et al., Neuentwicklung eines lumbalen bewegungserhaltenden Bandscheibenimplantates, Feb. 25, 2002.

English Translation of Burn et al., Neuentwicklung eines lumbalen bewegungserhaltenden Bandscheibenimplantates, Feb. 25, 2002.

Hudgins, Development and Characterization of a Prosthetic Intervertebral Disc, Hudgins, Georgia Inst. of Tech., Nov. 1998.

Kweon et al., Optimal Design of Synthetic Intervertebral Disc Prosthesis Considering Nonlinear Mechanical Behavior, Dec. 20, 2001.

* cited by examiner

PROSTHETIC INTERVERTEBRAL DISCS HAVING COMPRESSIBLE CORE ELEMENTS BOUNDED BY FIBER-CONTAINING MEMBRANES

FIELD

This description deals with a medical device, specifically a prosthetic intervertebral disc having a compressible core bounded by a fiber-containing or fiber-reinforced membrane.

BACKGROUND

The intervertebral disc is an anatomically and functionally complex joint. The native intervertebral disc is made up of three component structures: (1) the nucleus pulposus; (2) the annulus fibrosus; and (3) the vertebral end plates. The biomedical composition and anatomical arrangements within these component structures are related to the biomechanical function of the disc.

The spinal disc may be displaced or damaged due to trauma or a disease process. As a result of such displacement or damage, the nucleus pulposus may herniate and protrude into the vertebral canal or intervertebral foramen. That deformation is commonly known as a herniated or "slipped" disc. The deformation may press upon one or more of the spinal nerves exiting the vertebral canal through the partially obstructed foramen, causing pain or paralysis in its area of influence.

One method of alleviating this condition involves surgically removing the involved disc and fusing the two adjacent vertebrae. In this procedure, the removed disc is replaced by a spacer and secured to the neighboring vertebrae by screws, plates, and rods. Although "spinal fusion" evidences excellent short-term results, long-term studies show that the procedure eventually leads to degenerative changes in the spine, particularly at adjacent mobile segments. As a result of the fused segment's increased stiffness, adjacent discs incur increased motion and stress. In the long term, this change in the mechanics of the spine causes the adjacent discs to degenerate.

Prosthetic intervertebral discs are now used as alternatives to spinal fusion. Various artificial intervertebral disc designs are extant; many share the goal of mimicking the kinematics and load-sharing properties of the natural intervertebral disc. Two such design categories are ball-and-socket joint type discs and elastic rubber type discs.

Artificial discs of the ball-and-socket type usually include a pair of concave metal plates, one to be attached to the upper vertebra and the other to be attached to the lower vertebra, and a rounded core working as a ball. The concavities within the metal plates cooperate with and rotate with respect to the rounded core. The ball-and-socket type disc allows free rotation between the adjacent vertebrae between which the disc is installed. Such discs do not share any of the load placed on the spine as the spine bends.

In contrast, ball-and-socket discs have very high stiffness in the vertical (or compressive) direction, much higher than the normal compressive stiffness of the natural disc. As a result, although these discs allow flexion of the spine where a fused disc does not, the structure of these discs still causes adjacent discs to absorb extra compressive loads and still allow eventual and early degeneration of those discs.

Another common artificial disc design includes an elastic rubber or elastomeric polymer body embedded between a pair of metal plates. The disc is introduced into the emptied region between two adjacent vertebrae by affixing the two metal plates, via a surgical procedure, to those two vertebrae. The elastomeric polymer body is bonded to the metal plates through a rough, porous interface surface. This disc design is able both to absorb vertical, compressive shocks and to bear loads in that direction. However, the interface between the elastomeric polymer body and the metal plates is subject to peeling or severance due to the nature of the junction.

The prosthetic devices described here include a compressive core with gel or polymeric materials and a fiber-reinforced membrane forming the functional core periphery that, with proper application of our teachings, will match or approximate the functional characteristics of a healthy natural disc in its proper site in the spine.

SUMMARY

This description includes prosthetic intervertebral discs and methods for using such discs. The subject prosthetic discs include an upper end plate, a lower end plate, and a compressible core member situated between the two end plates. The active peripheral region includes a fiber-reinforced or fiber-containing membrane or skin, potentially integrated with the compressible core member. In general, the peripheral fiber-containing membrane actively cooperates with the core in biomechanically mimicking the constrained motion of a natural disc.

One variation of our described prosthetic disc includes top and bottom plates separated by a compressible core comprising one or more hydrogels or elastomers or both, substantially enclosed by a fiber-containing polymeric membrane. The fiber-containing polymeric membrane may be maintained in position in the prosthetic disc via fixation to the upper and lower plates by, at least, compression of the fiber-containing membrane between those end plates and cooperating adjacent plates provided for such purpose. The core may comprise a variety of different configurations comprising, e.g., single materials having a single composition, single materials having varied composition (perhaps with a nuclear region approximating the size the nucleus pulposus), multiple compositions, structural variations having fabric-defined volumes, baffled regions, fiber-infused gel or elastomeric regions, and the like. The cores may be preformed or formed in place.

Another variation of our described prosthetic disc also includes top and bottom plates separated by a compressible core comprising the materials discussed just above. In this variation, the fiber-containing polymeric membrane may be maintained in position in the assembled prosthetic disc via fixation to the upper and lower plates using a retaining groove.

Still another variation of the described disc comprises a subcomponent having a fiber-wrapped compressible core, where the core, before wrapping, includes upper and lower plates that are included within the wrapping. The plates include extensions or other attachments suitable for directly (or indirectly) attaching to the two adjacent vertebrae.

The described prosthetic discs may be used with separate vertebral body fixation elements or may include integrated vertebral body fixation elements. We also describe kits including our prosthetic discs and methods of using them.

BRIEF DESCRIPTION OF THE DRAWINGS

The Figures are not necessarily drawn to scale. Some components and features may be exaggerated for clarity.

DESCRIPTION

Described herein are prosthetic intervertebral discs and methods for making and using them. The prosthetic discs include top and bottom plates separated by a compressible element. The compressible element may include one or more annular elements or regions and a nuclear region or element. The compressible element or core is often configured to mimic the range of motion, compressibility, axis of rotation, and springiness of natural vertebral discs. In general, the compressible element in the described variations is bound by one or more fiber-containing boundary membranes. The interior of the compressible element in these variations may be compressible, polymeric gels having a single density or containing varying materials having several different densities are including flow restrictors such as baffles or the like. The interior of the compressible element in these variations may also comprise a portion that is a wrapped or woven to include other materials that cooperate to mimic the motion of a natural disc. The interior of the compressible element in these variations may also be molded prior to placement in the boundary membranes The described prosthetic discs may be employed in combination with a separate component having vertebral body fixation elements or the prosthetic discs may include integrated body fixation elements. The described prosthetic discs may also be employed in kits suitable for use by an orthopedic surgeon.

Prosthetic Intervertebral Disc

As mentioned above, the device we describe here is a prosthetic intervertebral disc. By the term "prosthetic intervertebral disc" we is mean an artificial or man-made device that is configured or shaped in such a way that it may be used as a replacement for an intervertebral disc in the spine of a vertebrate, e.g., a mammal such as a human. Our described disc may be varied in size, width, thickness, shape, and the like, to generally be appropriate for the opening left by the removal of a natural disc from a human spine. That is to say: our prosthetic intervertebral disc is of dimensions that permit it to substantially occupy the space between two adjacent vertebral bodies, where that space has been created when a naturally occurring disc between those two vertebrae has been removed. By the term "substantially occupy" we mean that the prosthetic intervertebral disc occupies at least 75% of the voided disk space. In general, our prosthetic intervertebral discs are structures that are somewhat bean-shaped (when viewed from above or below) and have the approximate shape of the naturally occurring intervertebral discs that they replace.

In most of our variations, the prosthetic intervertebral disc ranges in size, front to back, from about 15 mm to about 50 mm, perhaps from about 18 mm to about 45 mm. The width of the disc ranges, side to side, from about 12 mm to about 30 mm, perhaps from about 14 mm to about 25 mm. The height or thickness of the disc ranges from about 3 mm to about 13 mm, perhaps from about 5 mm to about 12 mm. Often, the top end plate is not parallel to the bottom end plate.

The described prosthetic intervertebral discs may include an upper (or top) end plate and a lower (or bottom) end plate, where the upper and lower end plates are separated from each other by the compressible element. Ideally, the combination of the end plates and the compressible element (with the outer fiber-containing membrane) provides a prosthetic disc that functionally mimics the operation of a natural spinal disc.

Figure 1:
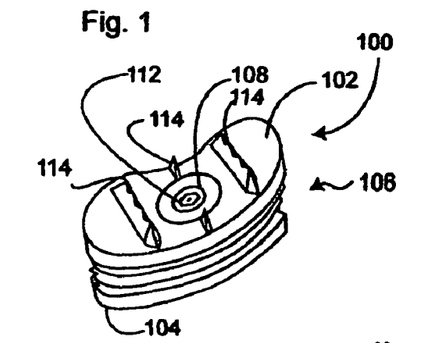
FIG. 1 is a perspective view of one variation of our prosthetic intervertebral disc.

FIG. 1 shows a front perspective view of a first of variation of our prosthetic intervertebral disc (100). Visible in this view are an upper (or top) outer end plate (102), and a lower outer end plate (104). The inner compressible element (106) may be seen between the upper and lower outer end plates (102, 104). It should be observed that the view of the prosthetic intervertebral disc (100) provides a somewhat bean-shaped structure similar to a natural disc. Also visible in this FIG. 1 is an extension (108) of the top inner end plate (110) (visible in FIG. 2) with its closure (112), e.g. a screwed-in plug, that may be used for filling the device (100) with a polymeric material. So-called "keel" members used in securing the device (100) to adjacent vertebrae may also be seen.

Figure 2:
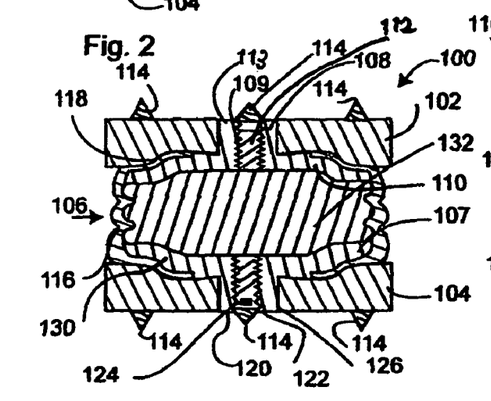
FIG. 2 is a cross section, side view of the prosthetic intervertebral disc variation shown in FIG. 1.

As is apparent from FIG. 1 and from the following Figures, the depicted variation includes cooperating inner end plates and outer end plates at opposite upper and lower ends of the device (100). As shown in FIG. 2, these cooperating end plates, e.g., outer top end plate (102) and top inner end plate (110), may be welded together at a junction (113) and also may be used to press and support the membrane (116) in the region (118). In this variation, cooperating end plates are desirable, but in other variations, such separate components of may not be as an unnecessary.

FIG. 2 shows, a cross-section, and side view of our prosthetic intervertebral disc (100). As noted just above, the depiction shows upper, outer end plate (102) with its associated keel components (114) and lower outer end plate (104) with its associated keel components (114). Also shown in this view is the bottom, inner end plate (107) having, as was the case with top, inner end plate (110), a fill port (122) having a closing plug (124). The closures or plugs (108, 124), as will be discussed below, may be used to fill the device with an appropriate material, e.g., a hydrogel. The bottom, outer end plate (104) and the bottom, inner end plate extension (120) may be welded, e.g., at the mating surface (126). Similarly, the outer, fibrous or fiber-containing membrane (116) may be maintained in position between bottom outer plate (104) and bottom inner plate (107) in region (130).

The complementary areas (118, 130) may also be used as sites for placement of adhesives usable variously in assembling the device and in providing stability to the overall structure once is deployed in maintaining the position of the exterior membrane (116).

The fibers may be woven into a fabric or mesh or gauze, as specifically shown in the drawings, or may be laid up in a random or non-random fashion in the membrane, with sufficient length and size, and proper composition as described below. When the fibers present in the exterior fibrous membrane (116) are clamped or otherwise held within the end plate assemblies, the fibers form part of the mechanical structure of the disc, both allowing physical motion similar to a natural disc and controllably constraining that motion in the same fashion.

Finally, core (132) provides, in cooperation with fibrous membrane (116), both compressibility and springiness. By choice of materials and constituent sizes, the core (132) within the outer membrane (116) also provides a measure of torsional freedom. That is to say that membrane (116) and core (132) allow top end plates (102, 110) to rotate a few degrees with respect to bottom end plates (104, 107). Such a range of rotation would be similar to that found in natural spinal discs.

Figure 3A:
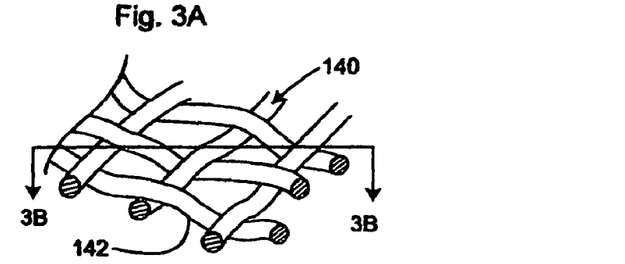
FIGS. 3A and 3B are, respectively, a schematic close-up view of a woven fabric and a cross section of a fibrous membrane containing that fabric, both useful in the device of FIG. 1.
Figure 3B:
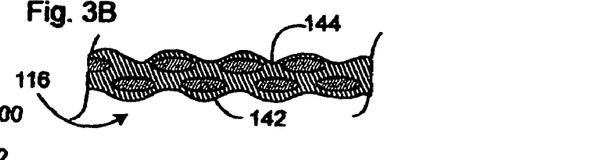

As noted above, the outer core membrane (116) may comprise one or more fibrous components and a polymeric covering or coating to produce a member that is substantially impermeable. FIG. 3A schematically depicts a woven fabric (140) having a number of fibrous elements (142). FIG. 3A shows a single layer of fabric (140). Membrane (116) may comprise one or more layers, if so desired. FIG. 3B shows a schematic cross-section of core membrane (116) with a number of fibrous components (142) in evidence.

Typically, the outer fibrous membrane (116) would comprise one or more layers of a simple woven material such as that found in FIG. 3A. Typically, the woven material would be produced in the form of a tube or sock-like structure. The tubes may be impregnated, infused, sprayed, dipped, or coated with a selected polymeric material (e.g., 144 in FIG. 3B) and placed in a mold form for additional curing. Such additional forming may take place in conjunction with the procedures discussed below. Generally, the top inner end plate (110) and the bottom inner end plate (107) will be placed within such a tube component prior to formation of fibrous membrane (116).

Figures 4A, 4B:
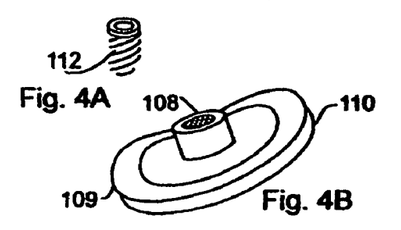
FIGS. 4A to 4D show perspective views of components of the FIG. 1 device.

FIGS. 4A to 4D show, in perspective view, several of the component pieces of our prosthetic disc (100). FIG. 4A shows closure (112). Closure (112) is shown as a simple plug at that may be inserted into the opening (109) found in an extension (108) of the top, inner end plate (110) shown in FIG. 4B. As noted below, opening (109) may be used for a variety of purposes in constructing our prosthetic disc (100). For instance, the opening (109) may be used to introduce one or more reacted or curable polymers into the interior of membrane (116) to form inner core (132). It may be used to produce an integrated inner core (132)—membrane (116) component.

Figures 4C, 4D:
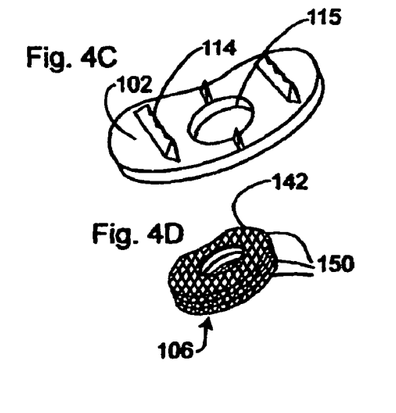

FIG. 4C shows top outer end plate (102) with its attendant keel members (114) and an opening (115) for accepting extension (108).

FIG. 4D shows a perspective view of inner core (106) (with the top inner end plate (110) and the bottom inner end plate (107) removed for explanatory purposes). Some fibrous members (142) are seen. The angles of fibrous members (142) with respect to the various top and bottom end plates may be varied to provide control of the resistance of the prosthetic disc to twisting. FIG. 4D also shows striations or grooves (150) in the exterior surface of fibrous membrane (116).

Figures 5, 7:
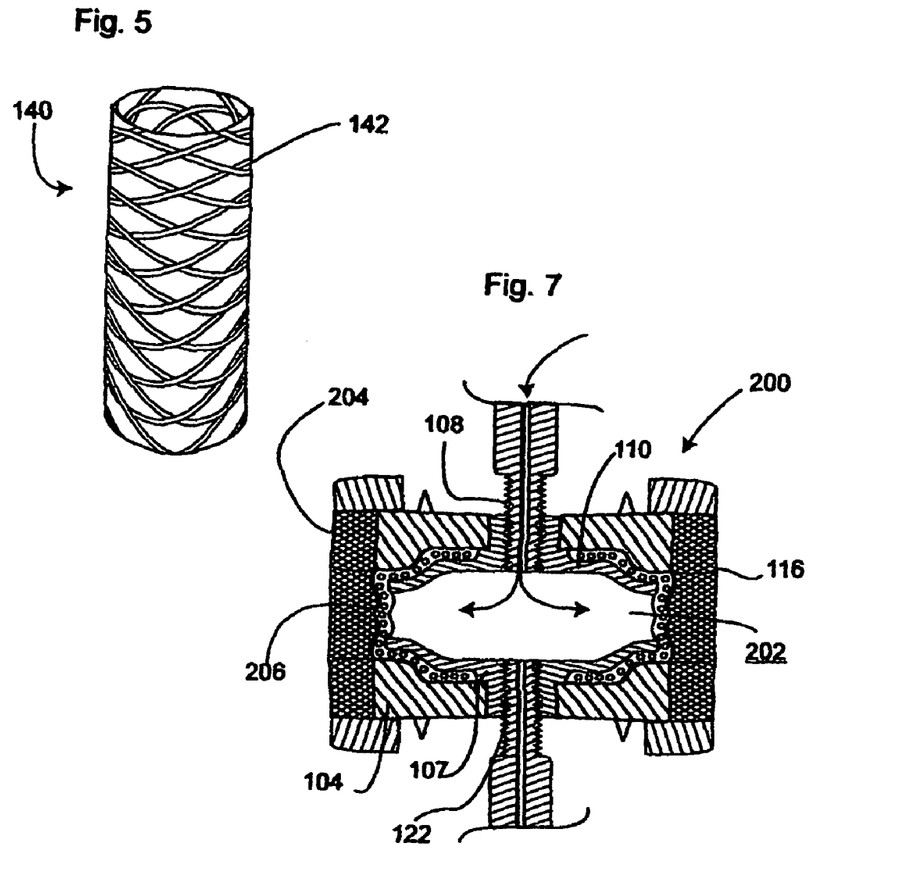
FIG. 5 is a perspective view of a woven fabric tube suitable for use in the FIG. 1 device.
FIG. 7 shows one variation of a molding apparatus suitable for forming the device of FIG. 1.

FIG. 5 shows a perspective view of woven tube (140) with fibrous members (142). As noted above, one or more such woven tubes may be placed concentrically in a fibrous membrane (e.g., (116) in FIG. 3B) as desired to assist in providing an appropriate level of torsional resistance to the prosthetic disc.

FIGS. 6A-6E provide a number of core structures suitable for use in our prosthetic disc as shown, e.g., in FIG. 2. Indeed, inner core (132) in FIG. 2 comprises a single material having some measure of compliance. The material of inner core (132) may be an elastomeric material, a gel, a hydrogel, or other compliant material providing compressibility to the prosthetic disc in conjunction with the outer membrane (116).

Figure 6A:
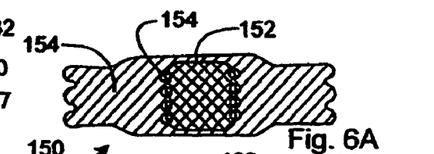
FIGS. 6A to 6E show variations of the core component suitable for use in the FIG. 1 device.

FIG. 6A shows a variation (150) of an inner core comprising a central component (152) similar to a natural nucleus in function, and comprising a lower viscosity material than that found in the annular region (154). In this variation of the inner core (150), the inner core material (152) may variously be a liquid, a gel (hydrogel), elastomeric, or solid. In the event that it is gel or liquid, the inner core material (152) may be enclosed by a substantially impermeable membrane, perhaps comprising a fabric (155) to isolate the inner core material (152) from the material if found in annular region (154). Indeed, in other variations of that depicted in FIG. 6A, the central region (152) may be free-floating or independent.

Figure 6B:
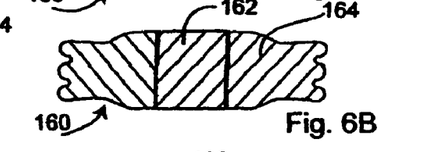

FIG. 6B shows a variation (160) of an inner core comprising a central component (162) and an annular region (164). Generally, the central component (162) and the annular component (164) would both be elastomeric in form. In this variation, the materials would be preformed together and introduced into the finished prosthetic disc rather than being formed therein.

Figure 6C:
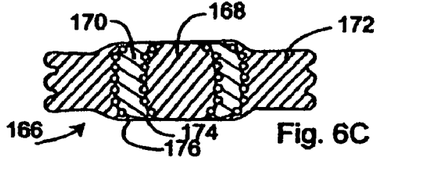

FIG. 6C shows a cutaway side view of another variation (166) having a central core region (168), an annular core region (170), and an outer core region (172). In this variation, the materials may be liquid or gels in central core region (168) and in annular core region (170). Depending upon the choice of materials, the barriers between central core region (168) and annular core region (170) and outer annular core region (172) may be impermeable or merely baffle-like in structure.

Figure 6D:
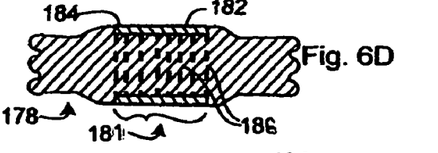

FIG. 6D shows a variation (178), a side view cutaway, in which a central region (181) is defined by one or more baffles. For instance, baffle (182) may be columnar and have slits (186). Similarly, outer baffle (184) may have a similar structure and be concentric about an inner baffle (182). This structure is particularly suitable when the material making up inner core (178) is a thixotropically flowable gel. Such baffles may be used in a variety of different configurations. Although the variation depicted in FIG. 6D shows generally columnar baffles him, other baffle structures are suitable depending upon the differential characteristics desired.

Figure 6E:
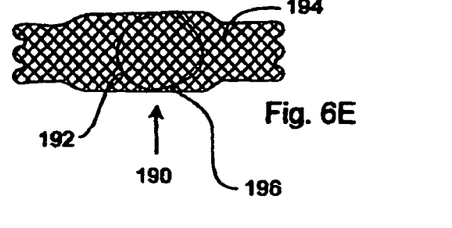

FIG. 6E shows another variation (190) in which the material making up the core includes a continuous matrix (192) and unconnected or loose fibers (194). The fibers are "unconnected" in the sense that they are not substantially connected to each other. In practice, fibrous material (194) may be interconnected to form a static three-dimensional solid. The fibers (194) may be treated so that they are adhesively connected to, and are reinforcements for, the continuous matrix (192). Whether the loose fibers (194) are connected to each other or are unconnected, they form an ad hoc, distributed baffle and they alter the local flow characteristics of the continuous matrix (192), particularly when the continuous matrix (192) comprises a gel. As is shown in FIG. 6E, the density of fiber distribution may be tailored so that the central region (196) may include a higher density of fibers thereby changing the localized flow characteristics of that portion of the central region (196).

FIG. 7 shows a cross-section, side view of an assembly (200) useful in producing at least this variation of our prosthetic disc. This assembly (200) includes components of the prosthetic disc itself (in particular, upper outer end plate (102), lower outer end plate (104), upper inner end plate (110), lower inner end plate (107), and fibrous membrane (116)). This assembly (200) is used to introduce polymeric material into the interior (202) or core region or, said another way, to mold or to fill the inner core space with one or more polymers and form at least some portion of the prosthetic disc's central core (e.g., (132) in FIG. 2, (150) in FIG. 6A, (160) in FIG. 6B, (166) in FIG. 6C, (178) in FIG. 6D, and (192) in FIG. 6E).

In particular, assembly (200) may be fabricated by dipping or spraying one or more sections of the woven tube (e.g., (140) in FIG. 5) with one or more selected polymeric materials, e.g., polyurethane(s) or silicone(s), and then placing the upper inner end plates (110) and the lower inner plates (107) within that polymer infused tube. Suitable adhesives may be placed on the surfaces of the upper inner end plate (110) and the lower inner end plate (107) facing the polymer infused tube. Such adhesives might, for instance, be chosen to react with or to be miscible with either or both of the polymeric materials used to infuse the outer membrane (e.g., (144) in FIG. 3B) and those chosen to form the central core. Examples of such adhesives include RTV and LSR type Silicones (available from Silicones Inc. and Dow Corning). Other adhesives compatible with other chosen polymers are similarly available. The surfaces of the upper inner end plate (110) and the lower inner end plate (107) facing the polymer infused tube (140) may also be selected to enhance adhesion between the plates (107, 110) and the fibrous membrane (116). Material selection and roughening steps are examples of such adhesion-enhancing selections.

Adhesives may be placed between the fibrous membrane (116) and the surfaces of the upper outer plate (102) and the lower outer plate (104) facing that fibrous membrane. Such surfaces may also be made to be adhesion enhanced.

The fiber-containing membrane (116) may be trimmed as necessary to properly fit the space between the inner and outer plates. The upper outer end plate (102) and the lower outer end plate (104) are placed in position as shown in FIG. 7. Where some type of central core structure (e.g., (152) in FIG. 6A, (168, 170) in FIG. 6C, and (182, 184) in FIG. 6D), that structure is usually introduced at this point. A clamping form (204) is used both to hold the various end plates in the depicted positions and to provide a molding form (206) against the fibrous membrane (116). The openings (108, 122) are used for injection of the selected polymer into the core volume (202). If needed, the chosen polymeric materials may then be cured or otherwise polymerized by heat.

The choice of polymers in this variation may allow the production of a core that is integrated with the polymer in the fiber-containing membrane and with any adhesive between the respective inner and outer plates. That is to say, for instance, that if the polymeric material infused into the fibrous membrane were a Silicone, a designer might desirably choose compatible Silicone-based adhesives for use between the fibrous membrane and the end plates and choose a Silicone-based hydrogel for the core.

Figure 8:
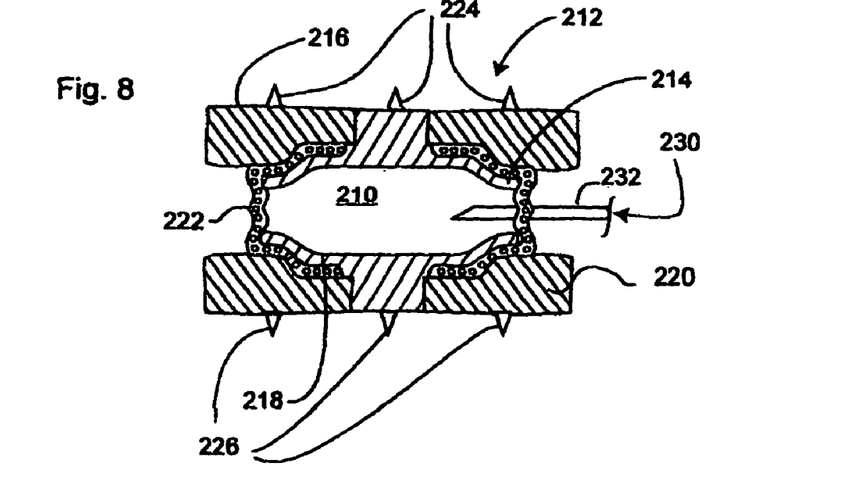
FIG. 8 shows a method for filling a prosthetic disc such as is found in FIG. 1 or 2 with a flowable polymer.

FIG. 8 shows another way in which flowable core polymers, e.g., gels and hydrogels, may be introduced into the core volume (210) of our prosthetic intervertebral disc. The empty prosthetic disc (212) may have been produced, for instance, in the manner outlined with respect to the device portrayed in FIG. 7, with the obvious exception that the core material is not yet introduced. The prosthetic disc (212) is depicted with an upper inner plate (214), upper outer plate (216), lower inner plate (218), and lower outer plate (220). The fibrous membrane (222) is also shown. The fibrous membrane (222) is fixedly clamped, as discussed above respectively between upper inner end plate (214) and upper outer end plate (216) at the upper end of the disc (212) and between lower inner end plate (218) and lower outer end plate (220). Keel components (224, 226) used for mounting in and adherence to suitably prepared, adjacent vertebrae are also found in this variation.

The polymeric core material (230) is injected through fibrous membrane (222) by use of a needle (232) until an appropriate amount is included. If a multiple component core, e.g., a core with a central component such as shown in certain of the variations discussed above, the central component may be introduced during an earlier fabrication step.

The fibrous membrane (222) and the end plates comprise a fillable prosthetic disc that may then be filled with core material either before the prosthetic disc is implanted or after.

Figure 9:
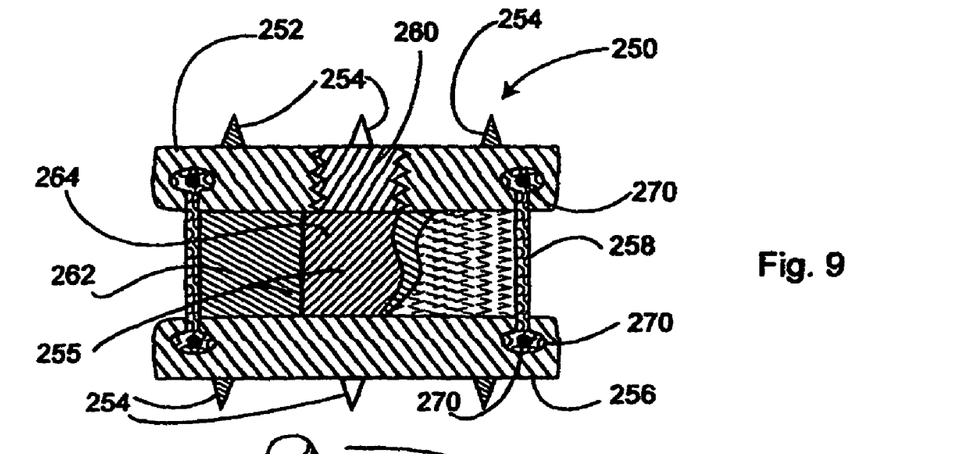
FIG. 9 shows a partial cutaway, side view of another variation of our prosthetic disc.

FIG. 9 shows, cross-section, a side view of another variation of our prosthetic intervertebral disc (250). The depiction of this variation shows an upper end plate (252) with its associated keel components (254) and lower end plate (256) with its associated keel components (254). This variation is shown not to have a separate inner end plate to secure the outer fibrous membrane (258) to the end plate. The manner of securing the outer fibrous membrane (258) to the end plates (252, 256) will be discussed in more detail below. Also shown is a filler plug (260) and corresponding opening through upper end plate (252) that is useful for filling the device with an appropriate material, e.g., a hydrogel.

The inner core (255) is shown as having an annular region (262) and a central region (264). As is the case with the other variations, the inner core (255) may be of the same types of materials.

Inner core (255) provides, in cooperation with fibrous membrane (258), both compressibility and springiness. By choice of materials and constituent sizes, the core (255) and the outer membrane (258) also allow a measure of torsional rotation similar to that found in natural spinal discs.

Figure 10:
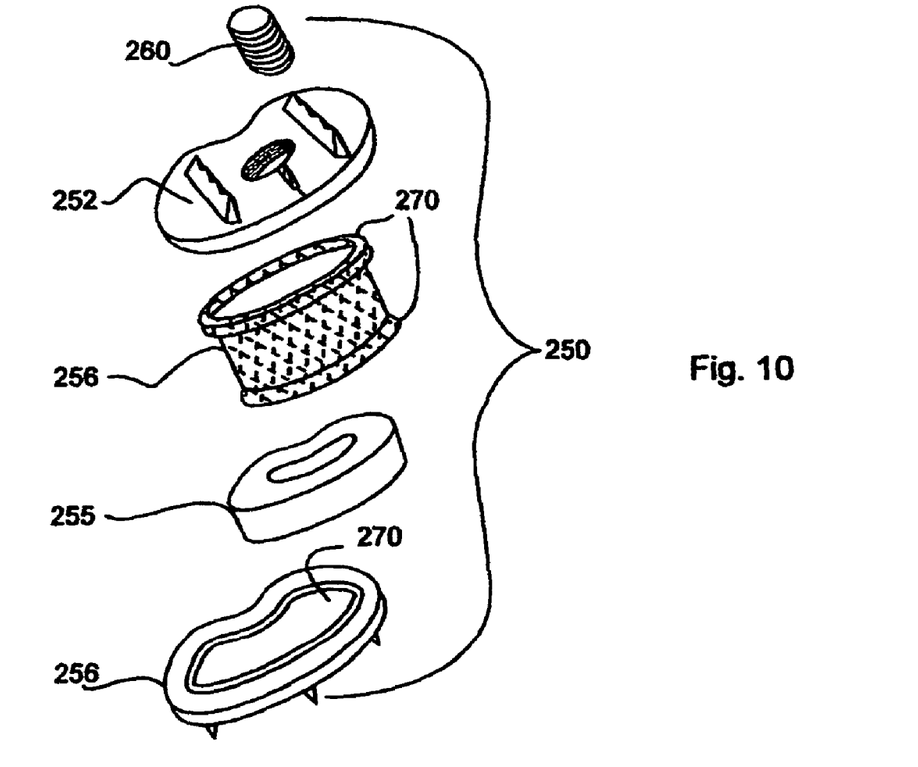
FIG. 10 shows an exploded view of the prosthetic disc shown in FIG. 9.

FIG. 10 is an exploded view of the prosthetic disc (250) shown in FIG. 9 showing the filler plug (260), upper end plate (252), fiber-containing membrane (256), inner core (255), and lower end plate (256). The upper and lower bead ring regions (270) on the fiber-containing membrane (256) may be seen. The upper and lower bead ring regions (270) are designed to fit into grooves (270) in the end plates (252, 256). As may be seen in the cross-sectional view in FIG. 9, the grooves may be wider at the depth of the groove than at the surface. The upper and lower bead ring regions (270) are configured to enter the groove (270), but not pull out. This may be done in a variety of ways. The fiber-containing membrane (256) may be layered in such a way that the thickness of the membrane varies and creates an interference fit with the ring (270 in FIG. 9) when the disc is fabricated.

Figure 11A:
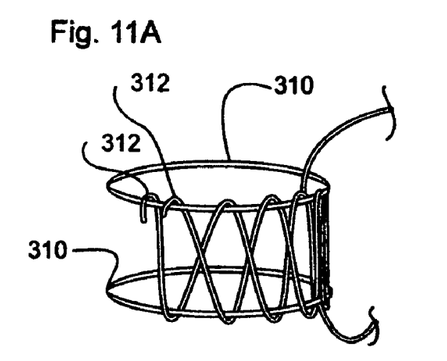
FIGS. 11A-11C show a procedure for fabricating the fiber-containing membrane as used in the prosthetic disc of FIGS. 9 and 10.
Figure 11B:
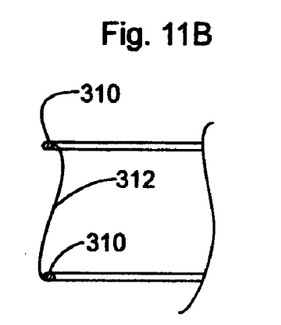
Figure 11C:
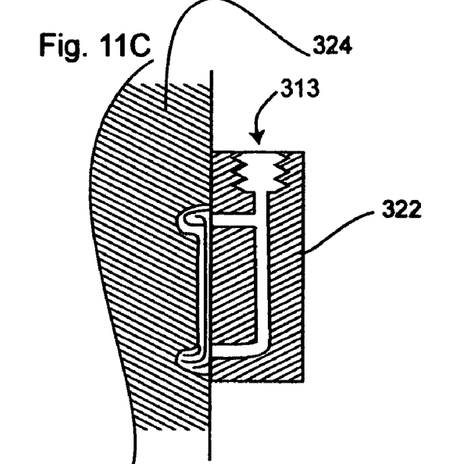

FIGS. 11A-11C shows a procedure for making a fiber-containing membrane (300 in FIG. 12) having a bead ring (302 in FIG. 9) suitable for fixing the membrane in the assembled end plate (304) of a prosthetic disc (306). Returning to FIG. 11A, a pair of generally flat bead rings (310) is wound with a desired pattern of fibers (312) perhaps in an in-and-out fashion as shown in the cutaway view shown in FIG. 11B. The bead rings are depicted to be smooth, but ridged or toothed rings are suitable for weaving fibers with more extreme and controllable angles—as measured between the fiber and the ring. A bead ring having openings through the flat portion of the ring for fiber weaving is also suitable.

Figure 11D:
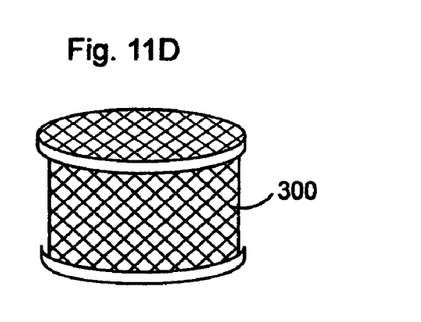
FIG. 11D shows the fiber-containing membrane produced by the procedure of FIGS. 11A-11C.

Once the subcomponent made up of the fiber (312) and rings (310) is complete, as shown in FIG. 11C, a polymer (313) may be injected into the subcomponent to form a membrane using, for instance, a circular mold having inner (322) mold and outer (324) mold parts creating a fibrous membrane (300) having the shape found in FIG. 11D.

Figure 12:
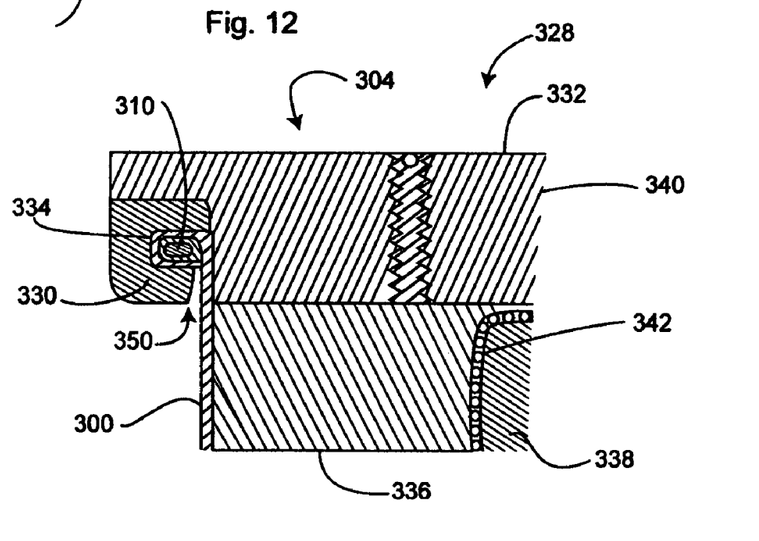
FIG. 12 is a cutaway, partial side view of an assembled end plate showing the securing of a tube-shaped, fiber-containing membrane of the type shown in FIGS. 11A-11C to that end plate.

FIG. 12 shows a cross section, side view of a prosthetic disc assembly (328) having an end plate (304) made up of an inner plate section (332) and an outer ring (330). The inner plate section (332) includes a filler plug (340) for filling the disc assembly with a flowable polymer. The inner core (336) is shown to include a central core member (338) surrounded by a fabric covering (342). Of special interest are the placement of the bead ring (310) within the inner groove (334) and the placement of that ring (310) around the inner plate section (332). The inner plate section (332) may be fastened to the outer ring (330) with screws (not shown) if needed. A clearance (350) is provided between inner plate section (332) and outer ring (330). However, the bead ring (310) and its surrounding woven fibers are too large to exit through the clearance area (350).

Figure 13:
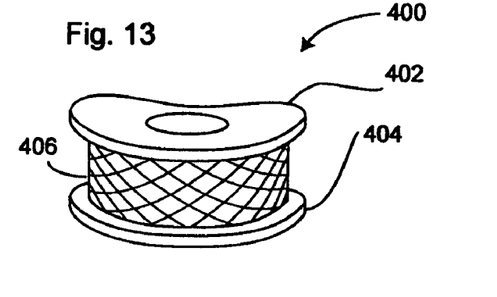
FIG. 13 is a perspective view of a variation of our prosthetic intervertebral disc.

FIG. 13 shows a perspective view of another variation of our prosthetic disc (400). The disc includes an upper end plate (402) and a lower end plate (404) separated by a central core (406) bounded by a fibrous membrane.

Figure 14:
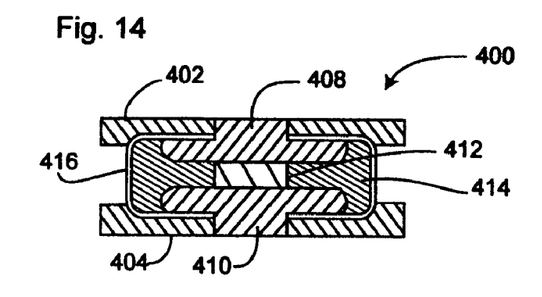
FIG. 14 is a cross section, side view of the prosthetic intervertebral disc variation shown in FIG. 13.

FIG. 14 provides a cutaway, side view of that prosthetic disc (400). The upper end plate (402) and lower end plate (404) have openings for the extensions of the upper (408) and lower (410) inner end plates. The inner end plates (408, 410) are typically welded to the outer end plates (402, 404). The inner core is shown to be made up of a center section (412) and an annular region (414) bounded by a fiber-containing membrane (416).

Figure 15:
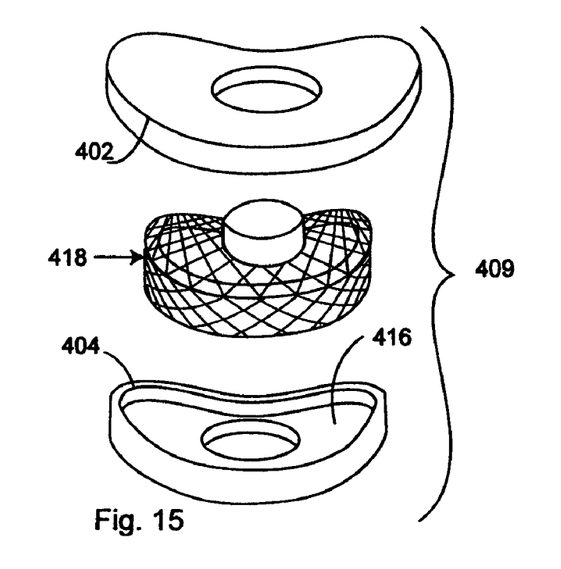
FIG. 15 shows an exploded view of the prosthetic disc shown in FIG. 13.

FIG. 15 shows an exploded view of the prosthetic disc (400) having the upper end plate (402) and the lower end plate (404). The optional recess (416) in the lower end plate (404) for receiving a pre-wound center core assembly (418) may be seen.

Figure 16:
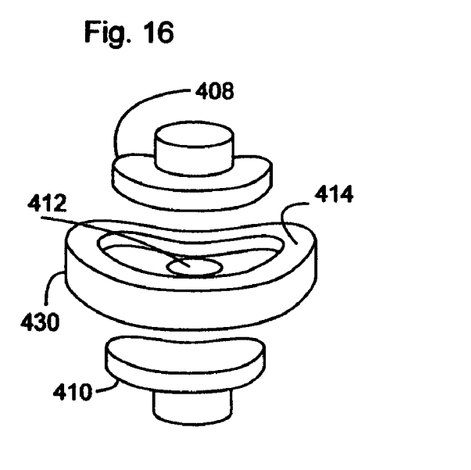
FIG. 16 shows an exploded view of some of the components of the core of the prosthetic disc shown in FIG. 13.
Figure 17:
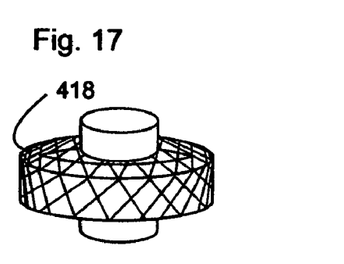
FIG. 17 is a perspective view of the core member of the prosthetic disc shown in FIGS. 13-15.

The pre-wound core assembly (418) may be assembled as shown in FIG. 16 from an upper inner end plate (408) and a lower inner end plate (410) surrounding a compressible core member (430) made of the central core member (412) and the annular member (414). The compressible core member (430) may include optional recesses for receiving the respective end plates.

The assembled subcomponent comprising the upper inner end plate (408), lower inner end plate (410), and compressible core member (430) is then wound with a fiber and infused, coated, dipped in, or sprayed with a polymeric material to form the membrane covering (416). The resulting pre-wound core assembly (418) shown in FIG. 16 is welded into the upper inner end plate (408) lower inner end plate (410).

Materials

Examples of the various materials of construction generically mentioned elsewhere are, without limiting the scope of such generic mention, are listed below.

Fibers

Suitable materials for preparing the various fibers include polyamides (e.g., various of the Nylon's), other polyesters such as polyethyleneterephthalate ("PET" commercially available as DACRON and HYTREL), various polyolefins such as polyethylene and polypropylene, as well as liquid crystal polymers available under the tradename VECTRA, polyaramid, Polyfluorocarbons such as polytetrafluoroethylene and e-PTFE, and carbon, metal, metallic alloy, or glass fibers. The fibrous components may be single strands or, more typically, multistrand assemblages. As a matter of design choice, the fibers generally have a high modulus of elasticity and possess high wear resistance. The fibers may have a modulus of elasticity at least about 100 MPa, perhaps at least about 500 MPa. The fibers may have a diameter that ranges from about 0.1 to about 5 mm, such as about 0.2 mm to about 2 mm.

Hydrogels

Hydrogels are water-swellable or water-swollen polymeric materials typically having structures defined either by a crosslinked or an interpenetrating network of hydrophilic homopolymers or copolymers. In the case of physical crosslinking, the linkages may take the form of entanglements, crystallites, or hydrogen-bonded structures to provide structure and physical integrity to the polymeric network.

Suitable hydrogels may be formulated from a variety of hydrophilic polymers and copolymers including polyvinyl alcohol, polyethylene glycol, polyvinyl pyrrolidone, polyethylene oxide, polyacrylamide, polyurethane, polyethylene oxide-based polyurethane, and polyhydroxyethyl methacrylate, and copolymers and mixtures of the foregoing.

Silicone-base hydrogels are also suitable. Silicone hydrogels may be prepared by polymerizing a mixture of monomers including at least one silicone-containing monomer and or oligomer and at least one hydrophilic co-monomer such as N-vinyl pyrrolidone (NVP), N-vinylacetamide, N-vinyl-N-methyl acetamide, N-vinyl-N-ethyl acetamide, N-vinylformamide, N-vinyl-N-ethyl formamide, N-vinylformamide, 2-hydroxyethyl-vinyl carbonate, and 2-hydroxyethyl-vinyl carbamate (beta-alanine). See, U.S. Pat. Nos. 5,079,319; 5,010,141; 5,451,617; and 5,962,548 for examples of silicone hydrogel preparation.

Elastomeric Materials

Examples of suitable representative elastomeric materials include silicone, polyurethanes, or polyester (e.g., Hytrel®).

Compliant polyurethane elastomers are discussed generally in, M. Szycher, J. Biomater. Appl. "Biostability of polyurethane elastomers: a critical review", 3(2):297 402 (1988); A. Coury, et al., "Factors and interactions affecting the performance of polyurethane elastomers in medical devices", J. Biomater. Appl. 3(2):130 179 (1988); and Pavlova M, et al., "Biocompatible and biodegradable polyurethane polymers", Biomaterials 14(13):1024 1029 (1993). Examples of suitable polyurethane elastomers include aliphatic polyurethanes, segmented polyurethanes, hydrophilic polyurethanes, polyether-urethane, polycarbonate-urethane and silicone-polyether-urethane.

Other suitable elastomers include various polysiloxanes (or silicones), copolymers of silicone and polyurethane, polyolefins, thermoplastic elastomers (TPE's) such as atactic polypropylene, block copolymers of styrene and butadiene (e.g., SBS rubbers), polyisobutylene, and polyisoprene, neoprene, polynitriles, artificial rubbers such as produced from copolymers produced of 1-hexene and 5-methyl-1,4-hexadiene.

We claim as our invention:

1. A prosthetic intervertebral disc comprising:
   i.) a top end and a bottom end plates separated by a compressible element, wherein the top end plate is metallic and comprises a top outer plate and a top inner plate and the bottom end plate is metallic and comprises a bottom outer plate and a bottom inner plate and where the top outer plate is welded to the top inner plate and the bottom outer plate is welded to the bottom inner plate,
   ii.) the compressible element separating the top and bottom end plates comprising at least one polymeric material and bounded between the end plates by at least one fiber-containing membrane having a polymeric covering or coating, the membrane being fixedly attached to the top end plate and the bottom end plate, and
   iii.) said at least one fiber-containing membrane having a polymeric covering or coating, the membrane being fixedly attached to the top end plate and the bottom end plate.

2. The prosthetic intervertebral disc of claim 1 where the at least one fiber-containing membrane is tubular and has an upper membrane end and a lower membrane end, wherein the top end plate comprises an outer plate and an inner plate and wherein the bottom end plate comprises an outer plate and an inner plate, and where the upper membrane end is fixedly attached to the top end plate by compression between the top end plate outer plate and the top end plate inner plate and where the lower membrane end is fixedly attached to the bottom end plate by compression between the bottom end plate outer plate and the bottom end plate inner plate.

3. The disc of claim 2 wherein the top end plate outer plate is welded to the extension of the top end plate inner plate and the bottom end plate outer plate is welded to the extension of the bottom end plate inner outer plate.

4. The prosthetic intervertebral disc of claim 1 where the compressible element comprises at least one flowable polymer.

5. The prosthetic intervertebral disc of claim 1 where the compressible element comprises at least one hydrogel.

6. The disc of claim 1 wherein the top and bottom end plates comprise mating surfaces for interfacing with upper and lower vertebral body fixation elements.

7. The disc of claim 1 wherein the top and bottom end plates further comprise integrated upper and lower vertebral body fixation elements.

8. A prosthetic intervertebral disc comprising:
   i.) a metallic top end plate comprising a top outer plate and a top inner plate having an axial extension configured to mate with the top outer plate and
   ii.) a metallic bottom end plate comprising a bottom outer plate and a bottom inner plate having an axial extension configured to mate with the bottom outer plate,
   iii.) a compressible element separating the top and bottom end plates, the compressible element comprising at least one polymeric material, and
   iv.) at least one fiber-containing membrane having a polymeric covering or coating, the membrane being fixedly attached to the top end plate and the bottom end plate, and
   where the fiber in the at least one fiber-containing membrane is wound in a substantially closed form about the compressible element and the top inner plate and the bottom inner plate, and wherein the at least one fiber-containing membrane is fixedly attached to the top end plate by compression between the top outer plate and the top inner plate and wherein the at least one fiber-containing membrane is fixedly attached to the bottom end plate by compression between the bottom outer plate and the bottom inner plate.

9. The prosthetic intervertebral disc of claim 8 where the compressible element comprises at least one flowable polymer.

10. The prosthetic intervertebral disc of claim 8 where the compressible element comprises at least one hydrogel.

11. The disc of claim 8 wherein the top and bottom end plates comprise mating surfaces for interfacing with upper and lower vertebral body fixation elements.

12. The disc of claim 8 wherein the top and bottom end plates further comprise integrated upper and lower vertebral body fixation elements.

13. The disc of claim 8 wherein the top end plate outer plate is welded to the extension of the top end plate inner plate.

14. A fillable prosthetic intervertebral disc comprising:
   i.) a top end plate comprising a top outer plate having an opening through the top outer plate and a top inner plate having an extension configured to mate with the opening in the top outer plate, the extension includes a channel with a first end and a second end, the first end adjacent the outer plate and sealed with a top plug,
   ii.) a bottom end plate comprising a bottom outer plate and a bottom inner plate,
   iii.) a fillable compressible element volume bounded by the top end plate and the bottom end plate and by at least one fiber-containing membrane having a polymeric covering or coating, the second end of the extension extending to the compressible element volume to provide access to the compressible element volume; and
   iv.) the membrane being fixedly attached to the top end plate and to the bottom end plate.

15. The fillable prosthetic intervertebral disc of claim 14 where the at least one fiber-containing membrane is tubular and has an upper membrane end and a lower membrane end, and where the upper membrane end is fixedly attached to the top end plate by compression between the top outer plate and the top inner plate and where the lower membrane end is fixedly attached to the bottom end plate by compression between the bottom outer plate and the bottom inner plate.

16. The disc of claim 14 wherein the top and bottom end plates comprise mating surfaces for interfacing with upper and lower vertebral body fixation elements.

17. The disc of claim 7 wherein the top and bottom end plates further comprise integrated upper and lower vertebral body fixation elements.

18. The disc of claim 14 wherein the top end plate outer plate is welded to the extension of the top end plate inner plate.

* * * * *